(12) United States Patent
Markwardt et al.

(10) Patent No.: US 8,295,570 B2
(45) Date of Patent: Oct. 23, 2012

(54) METHODS AND APPARATUS FOR MEASURING BODY CIRCUMFERENCE

(75) Inventors: Paul Markwardt, Verona, WI (US); Randall Payne, Madison, WI (US); Robert Washenko, Madison, WI (US)

(73) Assignee: General Electric Company, Schenectady, NY (US)

( * ) Notice: Subject to any disclaimer, the term of this patent is extended or adjusted under 35 U.S.C. 154(b) by 269 days.

(21) Appl. No.: 12/557,272

(22) Filed: Sep. 10, 2009

(65) Prior Publication Data

US 2011/0058725 A1  Mar. 10, 2011

(51) Int. Cl.
G06K 9/00  (2006.01)

(52) U.S. Cl. ............................. 382/128; 128/922; 378/4

(58) Field of Classification Search .................. 382/100, 382/128, 129, 130, 131, 132; 128/922; 378/4–27
See application file for complete search history.

(56) References Cited

U.S. PATENT DOCUMENTS

| | | | |
|---|---|---|---|
| 6,081,582 A | 6/2000 | Mazess et al. | |
| 6,088,615 A | 7/2000 | Masuo | |
| 6,198,797 B1 | 3/2001 | Majima et al. | |
| 6,442,287 B1 * | 8/2002 | Jiang et al. | 382/128 |
| 6,501,819 B2 * | 12/2002 | Unger et al. | 378/5 |
| 6,752,760 B2 | 6/2004 | Kouou | |
| 6,816,564 B2 * | 11/2004 | Charles et al. | 378/5 |
| 6,850,797 B2 | 2/2005 | Kawanishi et al. | |
| 6,853,741 B1 * | 2/2005 | Ruth et al. | 382/132 |
| 6,978,170 B1 | 12/2005 | Onda et al. | |
| 7,065,235 B2 | 6/2006 | Dewaele | |
| 7,196,332 B2 | 3/2007 | Wear et al. | |
| 7,343,192 B2 * | 3/2008 | Reiderman et al. | 600/410 |
| 7,421,104 B2 | 9/2008 | Hsieh et al. | |
| 7,561,726 B2 * | 7/2009 | Lu et al. | 382/128 |
| 2003/0065264 A1 | 4/2003 | Tsoref et al. | |
| 2006/0074288 A1 | 4/2006 | Kelly et al. | |
| 2008/0021349 A1 | 1/2008 | Sakai et al. | |
| 2008/0146961 A1 | 6/2008 | Okura et al. | |

OTHER PUBLICATIONS

Cao et al., Digital Hand Atlas and Web-Based Bone Age Assessment: System Design and Implementation, Computerized Medical Imaging and Graphics 24 (2000) 297-307.
Gertych et al., Bone Age Assessment of Children Using a Digital Hand Atlas, Computerized Medical Imaging and Graphics 31 (2007), 322-331.
Bertin et al., Measurement of Visceral Adipose Tissue by DXA Combined With Anthropometry in Obese Humans, International Journal of Obesity (2000) 24, 263-270.
Sabharwal et al., Computed Radiographic Measurement of Limb-Length Discrepancy. Full Length Standing Anteroposterior Radiograph Compared With Scanogram, The Journal of Bone & Joint Surgery (2006)88, 2243-2251.
Pietka et al., Computer-Assisted Bone Age Asessment: Graphical User Interface for Image Processing and Comparison, Journal of Digital Imaging vol. 17 No. 3 (2004) 175-188.

(Continued)

Primary Examiner — Anand Bhatnagar
(74) Attorney, Agent, or Firm — Fletcher Yoder, P.C.

(57) ABSTRACT

Methods and apparatus for measuring body circumference are provided. One method includes acquiring dual-energy two-dimensional (2D) scan information from a dual-energy x-ray scan of a body and generating a dual-energy image of the body using the 2D scan information. The method further includes determining a circumference of at least one portion of the body based on the dual-energy scan information and the generated dual-energy image.

18 Claims, 5 Drawing Sheets

OTHER PUBLICATIONS

Pieta et al., Integration of Computer Assisted Bone Age Assessment With Clinical PACS, Computerized Medical Imaging and Graphics 27 (2003)217-228.

Pietka, Computer-Assisted Bone Age Assessment Based on Features Automatically Extracted From a Hand Radiograph, Computerized Medical Imaging and Graphics vol. 19 No. 3 (1995) 251-259.

* cited by examiner

METHODS AND APPARATUS FOR MEASURING BODY CIRCUMFERENCE

BACKGROUND OF THE INVENTION

The subject matter disclosed herein relates generally to medical diagnostic imaging systems, and more particularly to diagnostic imaging systems that acquire bone and tissue images.

Body size measurements of an individual are commonly used to determine risk factors for potential diseases or conditions that can cause health problems. For example, waist circumference is a metabolic risk factor that is used as an anthropometric substitute for measuring abdominal fat. Waist circumference is commonly measured using a standard tape measure or other external gauge (e.g., bioelectrical impedance gauge). However, inter-observer and intra-observer variations in measurements using tapes measures or other external gauges may affect the validity of the measurements, leading to possible incorrect or inaccurate risk factor assessment. Moreover, it is often difficult to reproduce the exact measurement conditions (e.g., location of the measurements) during subsequent examinations, for example, during follow-up examinations. Accordingly, it may be difficult to accurately assess or determine changes in waist circumference. Additionally, some of the gauges use indirect estimators that are not focused on regions of interest, and accordingly, are not necessarily accurate for measurement of those regions.

In conventional external measurement methods for measuring the waist, the umbilicus is often used as a landmark. However, in larger or obese individuals, gravity can distend the umbilicus away from the equivalent vertebral position as compared to smaller or non-obese individuals. Moreover, other variations can occur in the conventional external measurement methods, for example, due to the amount of tension in the tape measure and the tendency of some individuals to suck in their abdomen when being measured.

BRIEF DESCRIPTION OF THE INVENTION

In accordance with one embodiment, a method for determining a circumference of a body is provided. The method includes acquiring dual-energy two-dimensional (2D) scan information from a dual-energy x-ray scan of a body and generating a dual-energy image of the body using the 2D scan information. The method further includes determining a circumference of at least one portion of the body based on the dual-energy scan information and the generated dual-energy image.

In accordance with another embodiment, a method for determining a circumference of a body is provided. The method includes acquiring bone information and soft tissue information from a dual-energy x-ray scan of a body and generating a dual-energy image of the body using the acquired bone information and soft tissue information. The method further includes identifying at least one portion of the body using the bone information displayed with the dual-energy image and determining a circumference of the at least one portion of the body using the soft tissue information acquired for the portion.

In accordance with yet another embodiment, a diagnostic imaging system is provided that includes a dual-energy x-ray bone densitometer configured to acquire bone information and tissue information from a dual-energy imaging scan of a subject. The diagnostic imaging system further includes a body circumference measurement module configured to measure a circumference of a portion of a body of the imaged subject using the acquired bone information and tissue information.

DETAILED DESCRIPTION OF THE INVENTION

Figure 1:
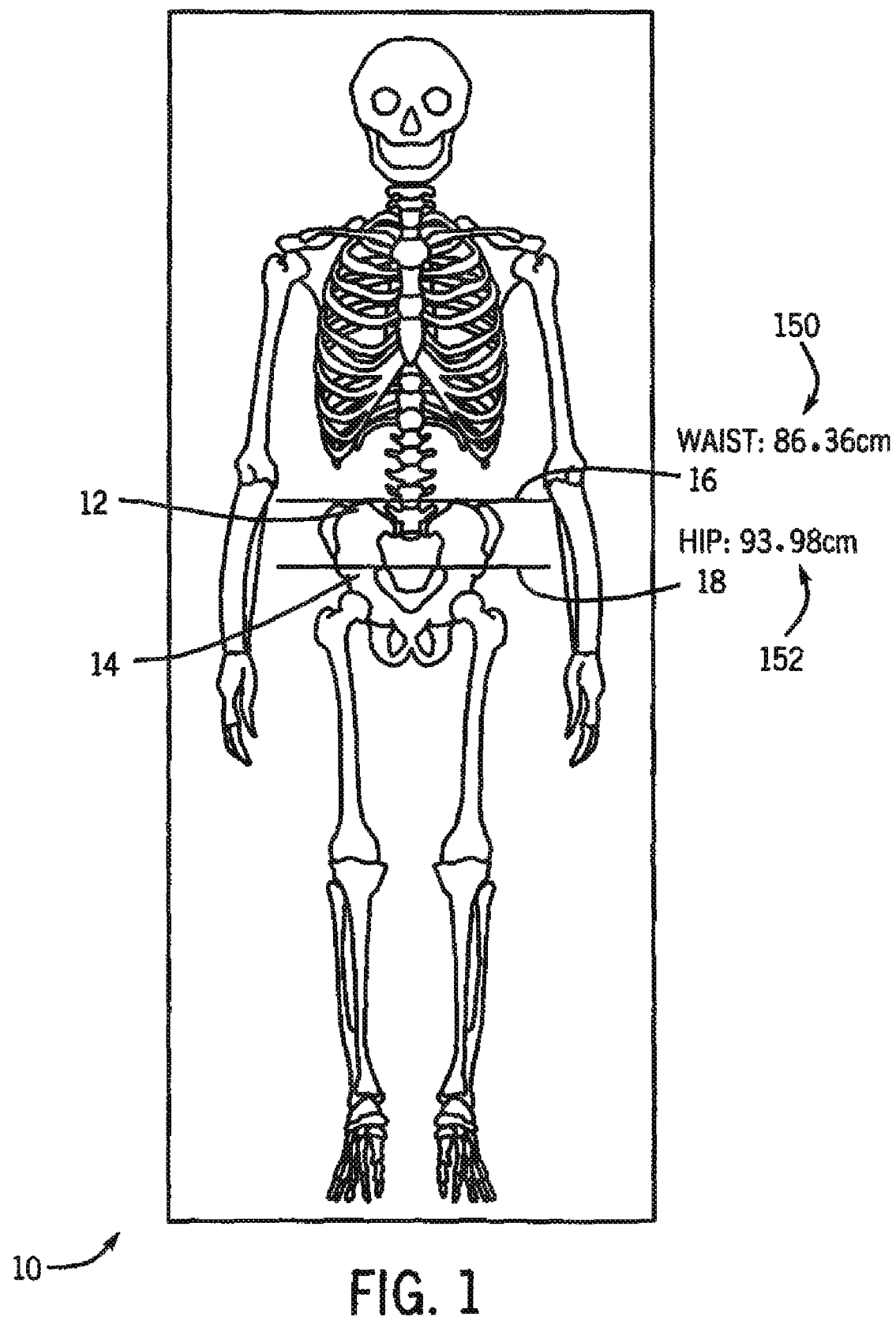
FIG. 1 is a dual-energy x-ray image acquired from a full body scan and used to determine body circumference measurements in accordance with various embodiments.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. One or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Exemplary embodiments of dual-energy x-ray systems and methods for scanning bodies to obtain bone and tissue information (particularly soft tissue information) are described in detail below. Various embodiments calculate body circumference, for example, waist and hip circumference measured from dual-energy x-ray scans of an imaged body. At least one technical effect of the various embodiments of the systems and methods described herein is to automatically determine the circumference of different portions of a body, for example, the circumference of a waist and hip of a body using dual-energy x-ray imaging. The acquisition of bone and tissue information during the dual-energy x-ray imaging allows for the determination of circumference measurements from two-dimensional (2D) planar scans of a body.

FIG. 1 is an image of a body (e.g., a patient's body), and more particularly, a full body dual-energy image 10 that may be generated from a scan of the entire body using a dual-energy x-ray system. The image is generated from a full body scan, which in some embodiments includes acquiring all bone and tissue information during a single scan, for example, a single imaging pass or operation. The total body scan may be acquired using different dual-energy imaging systems, for example, the Lunar iDXA imaging system available from GE Healthcare or other bone densitometer systems. An embodiment of a dual-energy x-ray imaging system is described in more detail below in connection with FIG. 2.

The image 10 allows for the identification of different portions or regions of the imaged body. For example, a waist 12 and a hip 14 of the imaged body can be determined using the image 10, for example, based on bone and tissue information in accordance with various embodiments as described below. The waist 12 and hip 14 are identified by lines 16 and 18, respectively, in FIG. 1. Each of the lines 16 and 18 may correspond to one or more image projections along the 2D imaged body shown in the image 10.

In general, the image formed from the dual-energy x-ray imaging system is a 2D image of a three-dimensional (3D) body. In particular, the image 10 is an anterior-posterior (AP) image of a vertebrae acquired using a dual-energy x-ray imaging system. The image may also be referred to a posterior-anterior (PA) image of vertebrae. The dual-energy x-ray system can be used to acquire both bone and tissue information (particularly soft tissue information) from one or more projection measurements of x-ray attenuation at two different x-ray energy ranges. For example, when a patient is lying down on a table between an x-ray source below the patent and an x-ray detector above patient (or vice versa), the detector can obtain information for a dual x-ray absorptiometry (DEXA or DXA) AP view of the spine, bones or a portion thereof as a result of the passage of x-rays at two different energy levels through the patient.

Figure 2:
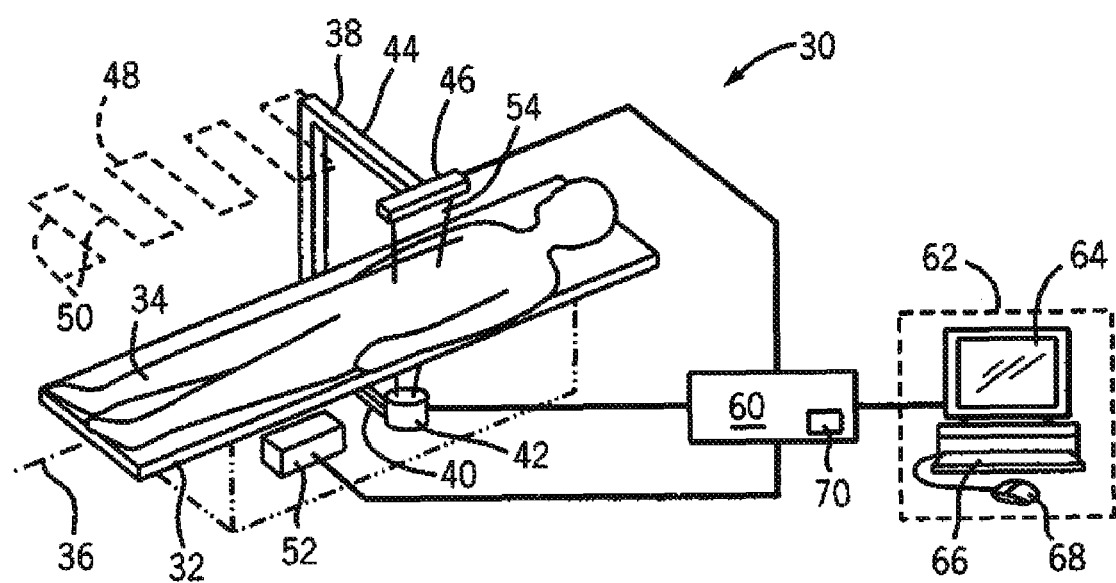
FIG. 2 is diagram illustrating a dual-energy x-ray imaging system formed in accordance with various embodiments illustrating a full body scan to acquire the image of FIG. 1.

FIG. 2 is a block diagram of an exemplary dual-energy x-ray system, illustrated as a dual x-ray absorptiometry (DEXA or DXA) system 30, which is also referred to as dual energy bone densitometer system capable of performing bone densitometry. The system 30 constructed in accordance with various embodiments is configured to measure at least an area of a bone, a length of a bone, a bone mineral content (BMC), a bone mineral density (BMD) and a tissue thickness. The BMD is calculated by dividing the BMC by the area of the bone. During operation, two x-ray beams having different energy levels are utilized to scan an object, for example, to scan a body of a human subject (e.g., a patient) to image the bones of the human subject. The acquired image(s), including bone information and tissue information from the imaged body, particularly determined tissue thickness information, is used to calculate a body circumference. The images may be generated in part from determined bone density information and tissue information acquired during a dual-energy x-ray scan.

The system 30 includes a patient table 32 providing a horizontal surface for supporting a subject, for example, a patient 34 in a supine or lateral position along a longitudinal axis 36. The system 30 also includes a support member, for example, a C-arm 38. The C-arm 38 has a lower end 40 that is positioned beneath the patient table 32 to support an x-ray source 42. The C-arm 38 has an upper end 44 that is positioned above the patient table 32 supporting an x-ray detector 46. However, it should be noted that the position of the x-ray source 42 and x-ray detector 46 may be reversed. The x-ray detector 46 may be fabricated, for example, as a multi-element cadmium-zinc-telluride (CZT) detector providing energy discrimination. The x-ray source 42 and the x-ray detector 46 may be moved in a raster pattern 48 so as to trace a series of transverse scans 50 of the patient 34 during which dual energy x-ray data is collected by the x-ray detector 46. The raster motion is produced by actuators (not shown) under control of a translation controller 52. During operation, the x-ray source 42 produces a fan beam 54 having a plane that is parallel to the longitudinal axis 36. However, in some embodiments, the fan beam 54 may be provided perpendicular to the longitudinal axis 36. The raster pattern 48 is adjusted in some embodiments such that there is some overlap (e.g., slight overlap of 10 percent) between successive scan lines of the fan beam 54.

The x-ray source 42, the x-ray detector 46, and the translation controller 52 communicate with, and are under the control of, a computer 60 which may include both dedicated circuitry and one or more processors having the ability to execute a stored program. In the exemplary embodiment, the computer 60 also includes a body circumference measurement module 70. The module 70 utilizes the scan data or the scanned image, and in particular, the acquired bone and tissue information to determine the circumference at different regions of a scanned body of the patient 34. During operation, the module 70 directs the dual-energy imaging system 30 to acquire a full body (or total body scan), from which certain bones may be identified, by identifying bone landmarks, as well as from which tissue measurements are made to determine tissue thickness. The locations of the landmarks may be determined automatically, manually or semi-automatically, for example, with an operator adjusting automatically generated landmarks.

The module 70 then utilizes the scan data or scan image(s), including the acquired bone and tissue information (particularly soft tissue information) to determine the circumference of different regions of the patient. In various embodiments, using bone and tissue information or measurements in combination with an elliptical model, body circumference is determined as described in more detail below. It should be noted that different landmarks may be used to identify different regions of interest for which the circumference is to be determined. It also should be noted that different models may be used to determine the circumference from the 2D planar scan from the imaging system 30. It further should be noted that although the various embodiments are described in connection with a dual-energy x-ray imaging system, the various embodiments are not limited to a dual-energy x-ray imaging system or a particular configuration thereof.

Referring again to FIG. 2, the computer 60 communicates with a terminal, such as a workstation 62 including a display 64, a keyboard 66, and a cursor control device such as a mouse 68 allowing for operator input and the output of text and images to the operator. In some embodiments, the computer 60 is located remotely from the workstation 62. Optionally, the computer 60 may form a portion of the workstation 62. The computer is adapted to perform one or more processing operations. The acquired bone and tissue information, for example, image, density and thickness information may be processed and displayed in real-time during a scanning session as the data is received. Additionally or alternatively, the data may be stored temporarily in a memory device on the computer 60 during a scanning session and then processed and displayed in an off-line operation. The information may also be stored in a long-term storage device (e.g., hard-drive or server) for later access, such as during a follow-up scan of the same patient and useful to monitor changes in the circumference of different measured body regions, for example, the waist and hip. The display 64 includes one or more monitors that present patient information, including the scanned image, including bone and tissue information to the operator for review, diagnosis and/or analysis. The displayed images may be modified and the display settings of the display 64 also manually adjusted using the keyboard 66, the mouse 68, or a touch screen icon on the display itself.

During operation, the system 30 is configured to operate in either a dual energy x-ray mode or a single energy x-ray mode. In the single energy mode, the x-ray source 42 emits x-rays at a narrow band of energies of a few keV and in the diagnostic imaging range of approximately 20-150 keV. In the dual-energy mode, the x-ray source 42 emits radiation at two or more bands of energy emitted simultaneously or in rapid succession. The x-ray source 42 may also be configured to emit a single broadband energy of more than a few keV over the diagnostic imaging range. The system 30 may be switched between the dual energy mode and the single energy mode by increasing or decreasing the x-ray source 34 voltage and/or current. The system 30 may also be switched between the dual energy mode and the single energy mode by removing or adding a K-edge filter. It should be noted that the x-ray source 42 may emit x-rays at different energies or ranges of energies.

The x-ray source 42 may be configured to output a fan beam of x-rays 54 as shown in FIG. 2. The x-ray source 42 may also be configured to output a pencil beam of x-rays (not shown), a cone beam of x-rays, or other configurations. In some embodiments, the module 70 controls the system 30 to operate in the single energy mode or dual-energy mode to acquire bone and tissue information to determine the circumference of different portions or regions of a scanned body. The dual-energy mode allows the acquisition of both skeletal bone information and tissue information, for example, soft tissue information, such as fat density information. Accordingly, the dual-energy mode allows for both skeletal and metabolic imaging of the patient 34 using attenuation information from the different energy levels. It should be noted that in the single energy mode, higher resolution images also may be generated.

Various embodiments provide for calculating the circumference of different portions or regions of a scanned body. The bone and tissue information used for calculating the circumference is acquired in the various embodiments using a single full body dual-energy scan. However, it should be appreciated that optionally region specific scans may be performed where only a portion or region of the patient 34 of interest is scanned for use in calculating one or more circumferences.

Figure 3:
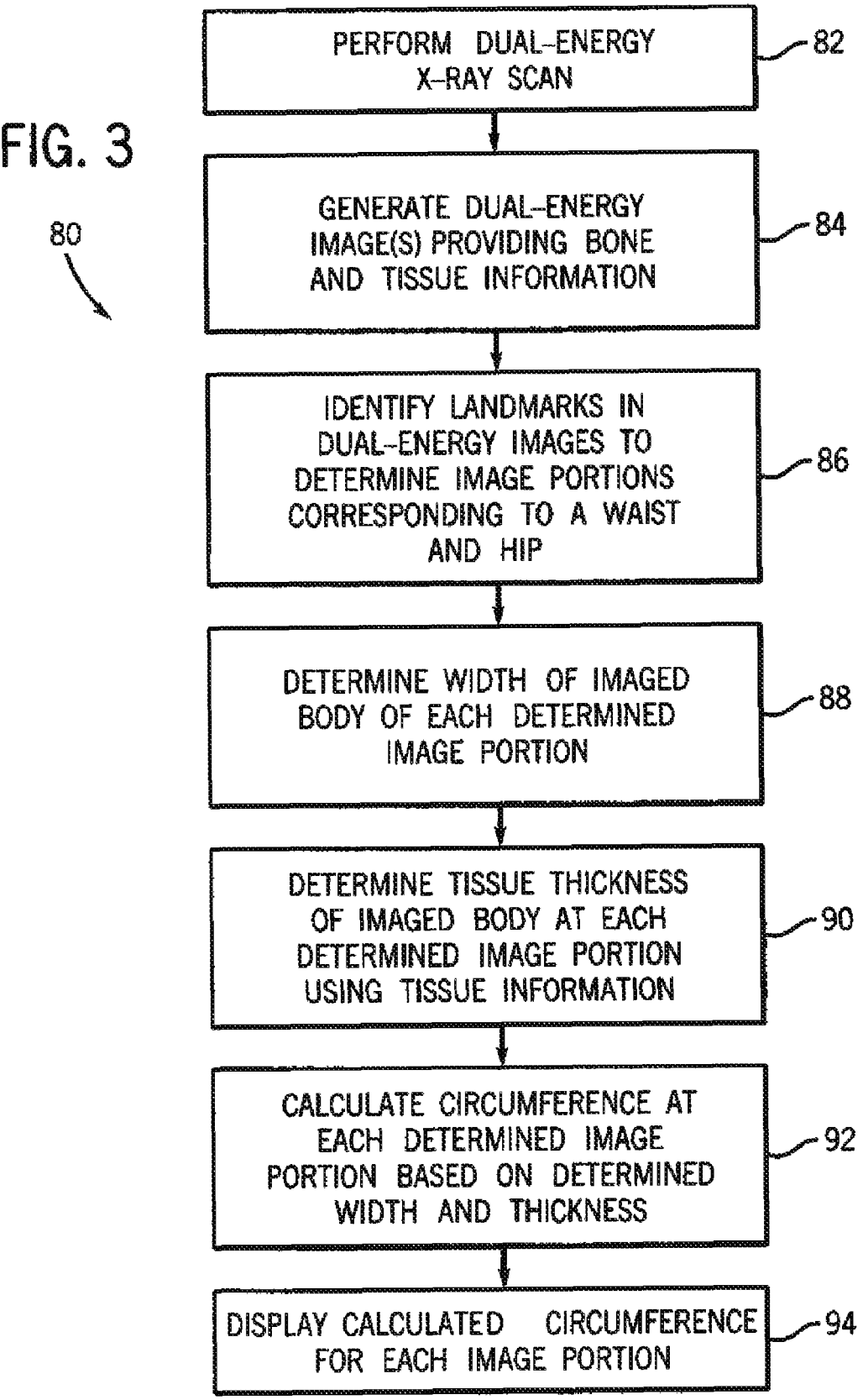
FIG. 3 is a flowchart of a method for calculating body circumference in accordance with various embodiments.

A method 80 for calculating body circumference is shown in FIG. 3. It should be noted that although the method 80 and the various embodiments are described in connection with calculating the body circumference of a particular body volume or body part, for example, the circumference of the waist of hip, the method 80 and the various embodiments may be used to calculate the circumference of any body volume or body part. For example, the method 80 and the various embodiments may be used to calculate the circumference of other human body parts, such as the legs or arms, or portions thereof.

The method 80 includes performing at 82 a dual-energy x-ray scan of an object, such as a patient or a portion of a patient. The patient in some embodiments lies supine on a table of a dual energy x-ray imaging system, such as a bone densitometer system. However, in other embodiments, the patient may be imaged with a bone densitometer system wherein the patient is imaged in a standing position or other position.

The dual-energy x-ray scan may be a rectilinear scan of the entire patient body, which may be performed in a raster-type scanning sequence as described in more detail herein. During the dual-energy x-ray scan an image of the entire skeleton of the patient may be acquired, which includes image information relating to the bones in the skeleton, as well as tissue information. For example, a dual energy detector receives a beam after the beam has passed through the patient to generate electrical signals indicating the attenuation of the beam by the patient within distinct first and second energy ranges. Images such as a bone density images, tissue images, particularly soft tissue images, or a combination thereof are produced based on the attenuation of the x-ray radiation in the first and second energy ranges. Thus, the dual-energy system allows not only the formation of a radiographic attenuation image, but also the mathematical analysis of the composition of the attenuating material by dual energy techniques. For example, dual energy techniques may be used that quantitatively compare the attenuation of radiation at two energies to distinguish between bone and soft tissue. In various embodiments, the dual-energy scan acquires dual-energy 2D (planar) scan information.

It should be noted that a full body or total body scan of the entire body may be performed as a single scanning operation, which may be a low dose mode scan. In some embodiments, instead of a full body or total body scan, individual smaller scans of regions of interest, for example, the region around the waist and hip, may be performed in single sweep or rectilinear scans.

Referring again to the method 80, thereafter one or more dual-energy images are generated at 84 with each containing bone information, for example, bone image information and bone content information, as well as soft tissue information, for example, fat content information, thereby providing body composition information. For example, an image 10 as shown in FIG. 1 may be generated from a scan of the entire body and includes both bone and soft tissue information. The bone and soft tissue information may be separately identified, for example, by setting different attenuation thresholds, such as an attenuation range that defines bone, soft tissue and air. The settings may be predetermined, determined by a user or adjusted by a user. Alternatively, one or more dual-energy region images may be generated, which are smaller than the full body dual-energy image 10.

Using the full body dual-energy image(s), landmarks are identified at 86 to determine portions of the image corresponding to regions of interest. For example, landmarks are identified that allow for locating one or more scan lines that encompass a region of interest, such as the waist and/or hip. It should be noted that the dual-energy image is composed of data of a variety of scan lines associated with each of the rays detected by the dual-energy system x-ray detector. Bone density and soft tissue information may be determined from the information corresponding to each of the scan lines, for example, attenuation information corresponding thereto. The measurements of each scan line produce measurements at a set of discrete pixels that represent a bone and soft tissue density along the ray line of that measurement. The bone and tissue density may be mapped to a gray scale to present an image to the operator.

The landmarks may correspond to different regions of interest and may be determined automatically, manually or semi-automatically. In some embodiments, landmarks are identified that are used to determine image portions (e.g., one or more scan lines) that correspond to a hip and waist of an imaged body. It should be noted that the landmarks are not limited to a particular kind or type of landmark, for example, a bone, but may be an area defined by soft tissue or other body elements. As an example, in embodiments where a waist region is to be identified, the various embodiments may identify the top of the iliac crest of the pelvis (identified in FIG. 1 by line 16) as determined from the imaged pelvis bone. For example, the iliac crest may be determined as the superior border of the wing of the ilium and the superolateral margin of the greater pelvis. In general, the iliac crest stretches posteriorly from the anterior superior iliac spine (ASIS) to the posterior superior iliac spine (PSIS).

The identification of the iliac crest may be performed in different ways. For example, the iliac crest may be determined manually by a user viewing a full body dual-energy image and placing a line (e.g., using a mouse) at the region of the image where the iliac crest is observed. It should be noted that the line may be defined by two endpoints or may be generated and then increased or decreased in length as needed, as well as moved or adjusted. Additionally, the line may encompass one or more scan lines or only one scan line. The iliac crest also may be identified automatically using any method, for example, a template matching method or by searching for the widest bone structure in the hip region and identifying the top of that bone structure. It should be noted that when the automatic identification method is used, a user may still adjust the identified location of the iliac crest, for example, by moving an automatically generated line. It also should be noted that any method may be used to determine the iliac crest and the identification thereof is not limited to the methods described above.

Continuing with the example, in embodiments where a hip region is to be identified, the various embodiments may determine the widest extent (or maximum lateral extent) of the hip region, for example, by determining the widest extent of the tissue (e.g., the soft tissue determined from the dual-energy x-ray scan) of the hip region. The hip region may be identified, for example, at a predetermined distance below the iliac crest or top of the pelvis or a predetermined distance above the top of the femur bone.

The identification of the hip region may be performed in different ways. For example, the hip region may be determined manually by a user viewing a full body dual-energy image and placing a line (e.g., using a mouse) at the region of the image where the hip region defined by the widest extent of the soft tissue is observed. It should be noted that the line may be defined by two endpoints or may be generated and then increased or decreased in length as needed, as well as moved or adjusted. Additionally, the line may encompass one or more scan lines or only one scan line. The hip also may be identified automatically using any method, for example, a pixel measuring method or slope change method.

In the pixel measuring method, the distance from one side of the imaged body to the other side is measured using a pixel count (as each pixel in the full body dual-energy image has a known size in the vertical and horizontal direction). The pixel count may start, for example, from a predetermined location as described above and move upward or downward (in a superior or inferior direction), namely longitudinally along the full body scan until a widest measurement is determined. The widest measurement may be determined at the point where the measurement changes from an increasing value to a decreasing value. In the slope change method, a similar process may be performed, except an identification of the hip is determined from a slope change (e.g., from a positive slope to a negative slope) of an outline of an exterior border of the image. It should be noted that when the automatic identification method is used, a user may still adjust the identified location of the hip region, for example, by moving an automatically generated line. It also should be noted that any method may be used to determine the hip region and the identification thereof is not limited to the methods described above.

Once the one or more regions of interest are identified, for example, once scan lines corresponding to the regions of interest are identified, such as the waist and hip region, a width of the imaged body is determined at each of the image portions thereof at 88. For example, the distance along the lines identifying the waist and hip regions is determined, such as by a pixel counting method. Accordingly, a distance laterally (e.g., from left side to right side) across the imaged body is determined.

It should be noted that, as described herein, the one or more regions may be different regions of the body. Thus, other body parts or volumes may be identified and measured.

Thereafter, a tissue thickness of the imaged body at each of the regions of interest, for example, corresponding to the identified scan lines is determined at 90. In various embodiments, using the soft tissue information from the dual-energy x-ray scan, a tissue thickness or profile along one or more scan lines may be determined. For example, using the soft tissue information from the dual-energy x-ray scan, a peak tissue thickness of the DXA soft tissue along the one or more lines may be determined. The peak tissue thickness then defines a distance across the imaged body, for example, from an anterior to a posterior of the body.

Figure 4:
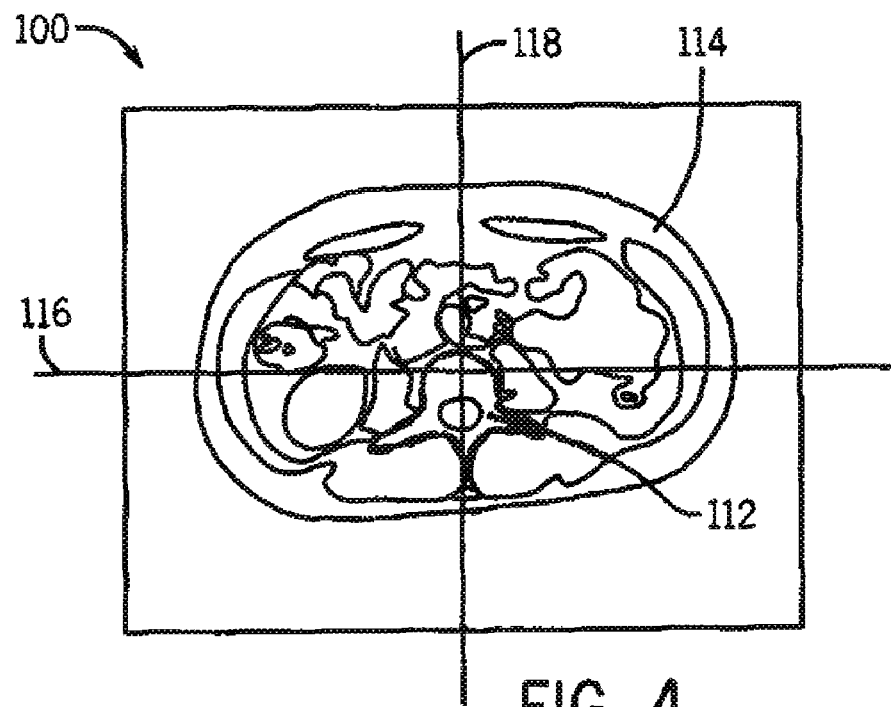
FIG. 4 is an image illustrating body content at a waist of a subject.
Figure 5:
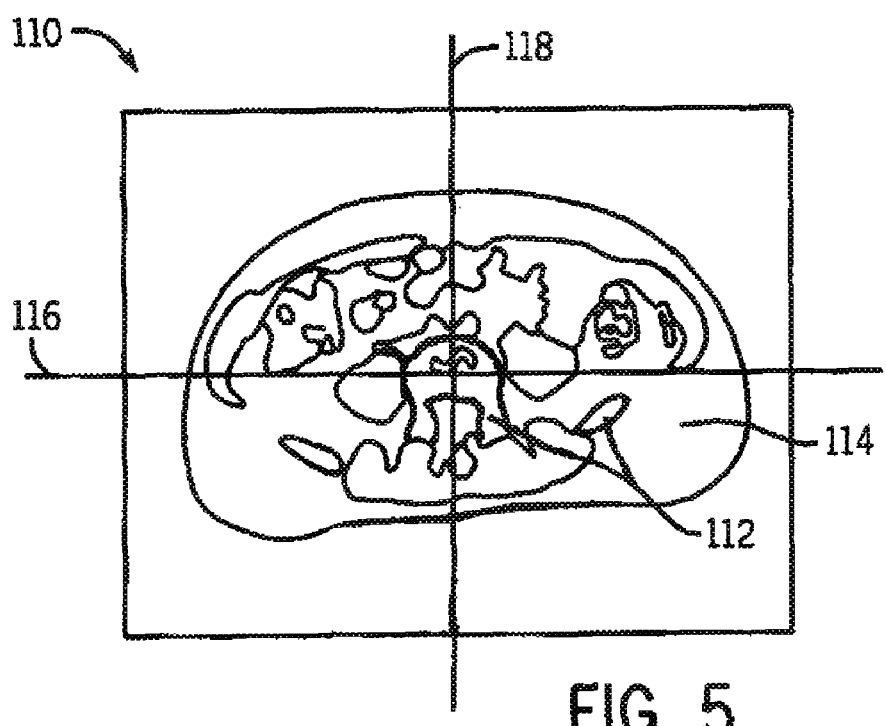
FIG. 5 is an image illustrating body content at a hip of a subject.

Thus, distances across two axes of the imaged body may be determined from planar DXA images. For example, images 100 and 110 illustrate body content at a waist and hip, respectively, of a human body and are shown in FIGS. 4 and 5 merely to illustrate the axes and body composition at the different regions. It should be noted that these cross-sectional images were not generated by a dual-energy x-ray imaging system, which as described above generates one or more 2D planar images of a body. However, using the dual-energy x-ray imaging system, bone information or images can be displayed and tissue thickness determined as described above. The images 100 and 110 illustrate that the width of the bones 112 and amount of soft tissue 114 (e.g., fat) changes at different regions of the body, for example, at the waist and hip, respectively. The body composition of each person is also different. Moreover, the cross-section of the body does not necessarily have a smooth or regular boundary that defines a particular shape. Thus, as shown, each of the images includes a first axis 116, namely a major axis (from side to side across the body) and a second axis 118 (from anterior to posterior), namely a minor axis.

Figure 6:
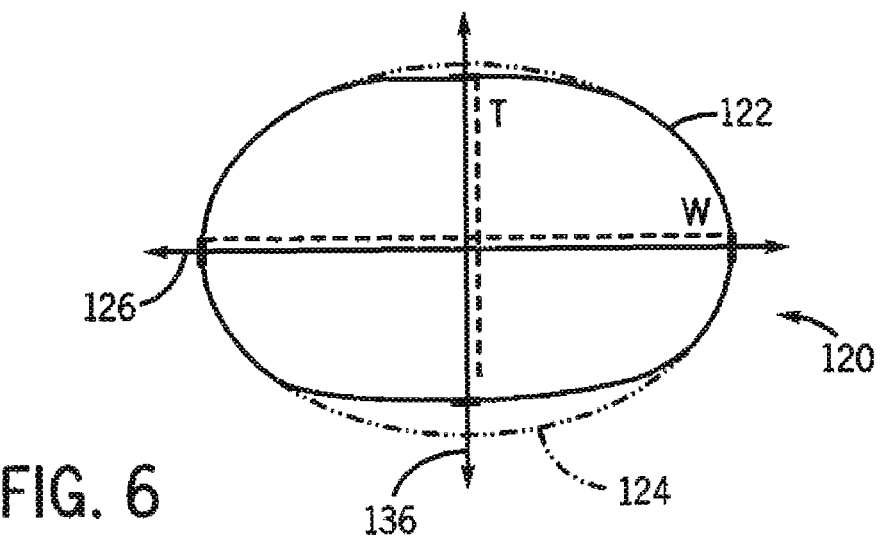
FIG. 6 is a diagram illustrating the use of an ellipse to approximate the cross-section of an imaged waist in accordance with various embodiments.
Figure 7:
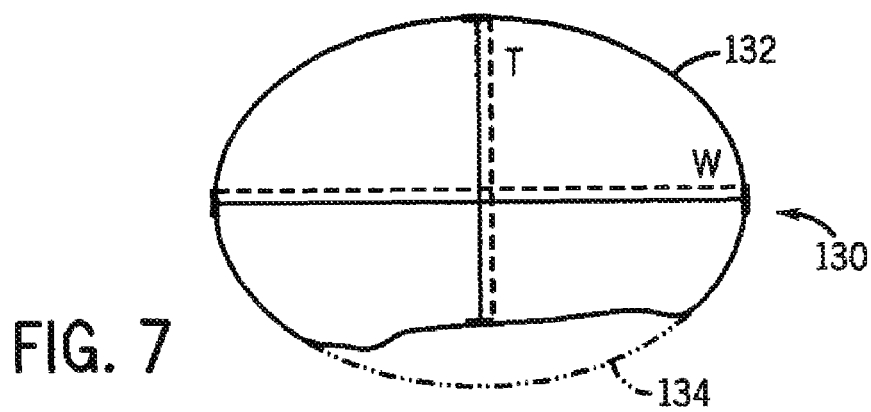
FIG. 7 is a diagram illustrating the use of an ellipse to approximate the cross-section of an imaged hip in accordance with various embodiments.

Referring again to the method 80, the circumference of the one or more regions of interest, for example, the waist and hip are calculated at 92 using the determined width and thickness as described above. In particular, as shown in FIGS. 6 and 7, a cross-section of the waist region 120 and a cross-section of the hip region 130, respectively, do not necessarily have a smooth, consistent and/or regular cross-section. For example, the cross-section of the waist region 120 and the cross-section of the hip region 130 may have a boundary 122 and 132, respectively that is irregular or non-elliptical. In accordance with various embodiments, using the determined width of the imaged body (identified by the line D in FIGS. 6 and 7) and the determined thickness of the imaged body (identified by the line T in FIGS. 6 and 7), the circumference is calculated by approximating or fitting an elliptical border 124 and 134, respectively, to each of the cross-sections. It should be noted that the elliptical borders 124 and 134 may be generated in any known manner, for example, by generating an elliptical shape using the measured width and thickness, which define a major axis 126 and 136, and a minor axis 128 and 138, respectively for the cross-sections of the waist region 120 and the cross-section of the hip region 130.

Figure 8:
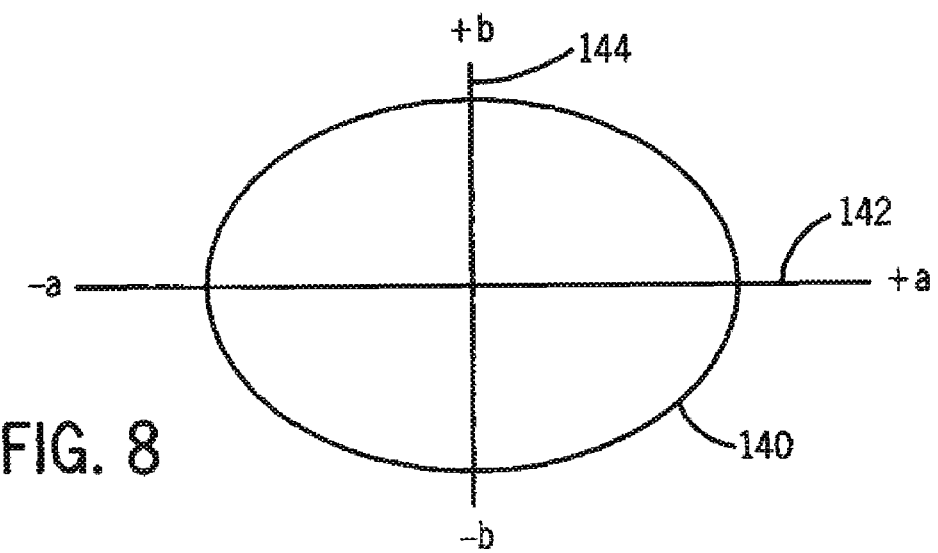
FIG. 8 is a diagram illustrating an ellipse of an elliptical model used to calculate body circumferences in accordance with various embodiments.

Accordingly, as shown in FIG. 8, the circumference of the one or more regions of interest may be calculated as the perimeter of an ellipse 140. The perimeter of the ellipse may be determined using mathematical calculations as are known that calculate the circumference either exactly or using approximations. Specifically, the perimeter of the ellipse may be calculated as follows (and as is knows): $4aF(\epsilon)$, where the function E is a complete elliptic integral of the second kind. In some embodiments, the perimeter may be calculated as follows: $(4a)*$integral (from 0 to Pi/2 of sqrt $\{(1-k^2(\sin(\theta))^2\}d(\theta)$, where $k=\{sqrt(a^2-b^2)\}/a$ and a and b are the axes 142 and 144, respectively.

The circumference may be also be approximated as the perimeter of the ellipse as follows: $2(Pi)sqrt \{(a^2+b^2)/2\}$, where a and b are the axes 142 and 144, respectively. It should be noted that any method known in the art may be used to calculate the perimeter of the ellipse 140.

Referring again to the method 80, after the perimeter of the ellipse has been calculated, which is the circumference of the one or more regions of interest, the calculated circumference(s) may be displayed at 94. For example, the calculated circumference(s) may be displayed adjacent the image portion corresponding to the region of interest. For example, the calculated circumference of the waist and hip may be displayed as values 150 and 152 adjacent the lines 12 and 14 (shown in FIG. 1), respectively.

Thus, various embodiments provide for calculating the circumference of one or more regions of a body (or a portion thereof) using dual-energy x-ray imaging, for example, from a DXA total body scan, which may be acquired using a low dose mode of operation of a bone densitometer. The circumference measurements may be used in combination with other bone density and body composition measurements. In some embodiments, the measurements are determined from a single low dose full body scan. For example, using the Lunar iDXA bone densitometer, the following scan exposures in Table 1 are typical (dependent on body size):

TABLE 1

| Site | Typical Scan Exposure* |
|---|---|
| DVA | 329 μGy |
| Spine | 146 μGy |
| Femur | 146 μGy |
| DualFemur | 146 μGy |
| Forearm | 10 μGy |
| Total Body | 3 μGy |

Moreover, typical scan times using the Lunar iDXA bone densitometer (dependent on body size) are in Table 2 as follows:

TABLE 2

| Site | Typical Scan Time* |
|---|---|
| DVA | 2 min. |
| Spine | 30 s |
| Femur | 30 s |
| DualFemur | 60 s |
| Forearm | 20 s |
| Total Body | 4 min. |

It should be noted that the shorter scan times, as well as the patient not knowing when the waist and hip regions are being imaged during the full body scan, reduces or eliminates the ability of patients to bias the waist measurement, such as by sucking in the abdomen. Additionally, when imaged in a supine position, reproducibility may be improved because posture and gravity effects on the abdomen and hips are standardized. In various embodiments, the DXA circumference measurements correlate well with other measurement methods.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for determining a circumference of a body, the method comprising:
    acquiring dual-energy two-dimensional (2D) scan information from a dual-energy x-ray scan of a body;
    generating a dual-energy image of the body using the 2D scan information; and
    determining a circumference of at least one portion of the body based on the dual-energy scan information and the generated dual-energy image by using an elliptical model for a cross-section of the at least one portion of the body to determine the circumference of the at least one portion.

2. A method in accordance with claim 1 further comprising identifying the at least one portion of the body using landmarks in the dual-energy image.

3. A method in accordance with claim 1 further comprising performing a full body dual-energy scan to acquire the 2D scan information.

4. A method in accordance with claim 1 further comprising performing a full body dual-energy scan of a subject in a supine scan position of a bone densitometer to acquire the 2D scan information.

5. A method in accordance with claim 1 wherein the 2D scan information comprises 2D planar anterior-posterior dual-energy scan information of the body.

6. A method in accordance with claim 1 wherein the 2D scan information comprises body composition scan information.

7. A method in accordance with claim 1 wherein the at least one portion of the body comprises one of a waist of the body and a hip of the body.

8. A method in accordance with claim 7 wherein a waist of the body is identified by a top of an iliac crest bone of a pelvis in the dual-energy image and the hip is identified as a widest portion of the dual-energy image in a hip region.

9. A method in accordance with claim 1 wherein the dual-energy scan information comprise bone information and soft tissue information.

10. A method in accordance with claim 9 wherein the at least one portion is identified using the bone information.

11. A method in accordance with claim 9 wherein the circumference is determined at least in part using a tissue thickness determined from the soft tissue information.

12. A method for determining a circumference of a body, the method comprising:
    acquiring bone information and soft tissue information from a dual-energy x-ray scan of a body;
    generating a dual-energy image of the body using the acquired bone information and soft tissue information;
    identifying at least one portion of the body using the bone information displayed with the dual-energy image; and
    determining a circumference of the at least one portion of the body using the soft tissue information acquired for the portion and using an elliptical model to determine the circumference of the at least one portion of the body, wherein a tissue width defines a diameter of one axis of an ellipse of the elliptical model and a peak tissue thickness defines another axis of the ellipse.

13. A method in accordance with claim 12 further comprising identifying at least one portion of the body using the soft tissue information.

14. A method in accordance with claim 12 wherein the tissue width is obtained from the dual-energy image and the peak tissue thickness is obtained from the soft tissue information for the at least one portion of the body.

15. A method in accordance with claim 12 further comprising performing a total body dual x-ray absorptiometry scan of the body to acquire the bone and soft tissue information.

16. A method in accordance with claim 12 further comprising performing a single rectilinear dual-energy scan of the body to acquire the bone and soft tissue information.

17. A diagnostic imaging system comprising:
    a dual-energy x-ray bone densitometer configured to acquire bone information and tissue information from a dual-energy imaging scan of a subject; and
    a body circumference measurement module configured to measure a circumference of a portion of a body of the imaged subject using the acquired bone information and tissue information and using an elliptical model for a cross-section of the portion of the body to determine the circumference of the portion.

18. A diagnostic imaging system in accordance with claim 17 further comprising a display displaying a dual-energy image generated from the acquired bone information and tissue information and having identifiable landmarks for use in determining the portion of the body to measure the circumference thereof.

* * * * *